United States Patent
Kaladelfos

(10) Patent No.: US 7,175,591 B2
(45) Date of Patent: Feb. 13, 2007

(54) TREATMENT OF VAULT PROLAPSE

(76) Inventor: George Kaladelfos, 17 Brighton Avenue, Toronto, New South Wales 2283 (AU)

( * ) Notice: Subject to any disclaimer, the term of this patent is extended or adjusted under 35 U.S.C. 154(b) by 141 days.

(21) Appl. No.: 10/473,375

(22) PCT Filed: Mar. 27, 2002

(86) PCT No.: PCT/AU02/00369

§ 371 (c)(1),
(2), (4) Date: Mar. 8, 2004

(87) PCT Pub. No.: WO02/078552

PCT Pub. Date: Oct. 10, 2002

(65) Prior Publication Data

US 2004/0138747 A1  Jul. 15, 2004

(30) Foreign Application Priority Data

Mar. 28, 2001  (AU) ................. PR4065

(51) Int. Cl.
A61F 13/00 (2006.01)
A61B 17/08 (2006.01)

(52) U.S. Cl. .................. 600/37; 600/30; 606/151
(58) Field of Classification Search ............... 600/29, 600/30, 37; 606/151; 623/13.11, 13.1
See application file for complete search history.

(56) References Cited

U.S. PATENT DOCUMENTS

| 4,428,375 A | 1/1984 | Ellman |
| 4,668,233 A | 5/1987 | Seedhom et al. |
| 5,919,232 A | 7/1999 | Chaffringeon et al. |
| 5,934,283 A * | 8/1999 | Willem et al. ............... 128/885 |
| 6,039,686 A | 3/2000 | Kovac |
| 6,042,534 A * | 3/2000 | Gellman et al. ............... 600/30 |
| 6,517,578 B2 * | 2/2003 | Hein ........................ 623/13.13 |
| 6,695,855 B1 * | 2/2004 | Gaston ....................... 606/151 |
| 6,808,487 B2 * | 10/2004 | Migliari ....................... 600/30 |
| 2002/0099259 A1 * | 7/2002 | Anderson et al. .............. 600/29 |
| 2003/0065402 A1 | 4/2003 | Anderson et al. |

FOREIGN PATENT DOCUMENTS

| EP | 1 078 601 A2 | 2/2001 |
| WO | WO 93/15690 A2 | 8/1993 |
| WO | WO 00/27304 A1 | 5/2000 |
| WO | WO 00/64370 A1 | 11/2000 |
| WO | WO 200106951 A1 * | 2/2001 |

* cited by examiner

Primary Examiner—Eduardo C. Robert
Assistant Examiner—Thomas J. Sweet
(74) Attorney, Agent, or Firm—Stinson Morrison Hecker LLP

(57) ABSTRACT

Apparatus for forming an artificial tie or ligament between different internal parts within a mammalian body, the apparatus comprising a strip (10) of preferably mesh type fabric formed of a material which is suitable for remaining in the body, and a drawstring (12) which is looped between different points along the length of the strip (10). By drawing the drawstring (12) the length of the strip (10) can be reduced. Opposite ends of the strip (11, 13) are in use attached to the different internal parts, and then those parts can be pulled together by applying tension to the drawstring (12), and once the length of the strip (10) has been reduced, tying off the drawstring (12) to hold the strip (10) in its reduced length condition. The apparatus is specifically useful for use in a in a method of treating vault or vaginal prolapse. The invention extends to a method of treating vault or vaginal prolapse.

16 Claims, 2 Drawing Sheets

TREATMENT OF VAULT PROLAPSE

CROSS-REFERENCE TO RELATED APPLICATIONS

This application is a national phase application and claims priority from PCT Application. No. PCT/AU02/00369, filed on Mar. 27, 2002, which claims priority from Australian Patent Application No. PR 4065, filed on Mar. 28, 2001. Both applications are hereby incorporated by reference in their entirety.

FIELD OF THE INVENTION

This invention relates to the treatment of vaginal or vault prolapse and to a device suitable for use in such treatment. The device might be used in other medical procedures.

BACKGROUND OF THE INVENTION

Vault or vaginal prolapse is a condition which occurs in women who have undergone a medical procedure such as a hysterectomy which has resulted in the utero-sacral ligaments which hold the vagina in position within the body cavity being severed or damaged. The result of such damage is that the vagina has a tendency to invert which is uncomfortable and unhealthy, and renders the vagina unsuitable for intercourse.

The condition has in the past been treated using one of various different procedures. Abdominal colposacropexy for example involves abdominal surgery which is undesirable. Zacharin's abdominal operation is another documented procedure in which the vagina is attached directly to the pelvic floor. Vaginal enterocole repair involves the attachment of the vault to the ileococcygeus muscle followed by posterior repair. Petros' infra-coccygeal sacropexy uses a nylon tape to "recreate" the utero-sacral ligaments.

Procedures performed via abdominal incision are particularly invasive and therefor not the preferred form of treatment. Procedures performed vaginally are however difficult to perform due to the close confines in which the procedure needs to be performed and the narrow passageway through which the surgeon must operate. It will be appreciated that attaching the distal end of the vagina to the pelvic floor in such a manner that the vagina is properly aligned and that the artificial ligaments thus created are of correct length and tension requires a great deal of skill and dexterity. An aim of the present invention is to facilitate the aforementioned vaginal procedure.

SUMMARY OF THE INVENTION

In broad terms the invention comprises a strip of fabric or mesh formed of a material adapted to remain within the body cavity after a procedure has been performed therewith, the strip incorporating a drawstring which extends between at least two points separated lengthwise along the strip, the drawstring being configured such that tension applied to the drawstring will assist in causing the length of the strip between the two points to be reduced.

Preferable the invention provides apparatus for forming an artificial tie or ligament between a first internal part, and a second, different, internal part, within a mammalian body, the apparatus comprising a strip of flexible material adapted to remain within the body after a procedure has been performed therewith, the strip incorporating a drawstring which extends between at least two points separated lengthwise along the strip, the drawstring being configured such that when one point has been attached to a first internal part of the body, and the other part point has been attached to a second internal part of the body, a tension applied to the drawstring will assist in causing the length of the strip between the two points to be reduced, and retain the strip in its reduced length condition, thereby forming said artificial tie or ligament between said first and second parts.

The strip is preferably made of a light mesh formed of an absorbable or non-absorbable thread. Suitable material might comprise proprietary materials such as Vypro™ or Prolene™ or Vycral™. The mesh openings are probably between 1 mm and 8 mm in diameter.

The drawstring is preferably threaded in and out, through the mesh openings, so that tension applied to the drawstring will tend to cause the strip to adopt a gathered configuration. The drawstring is preferably threaded in such a manner that the two ends of the drawstring are aligned parallel with each other and aligned with the length of the strip, the two ends being adapted to be tied together to retain the strip in its reduced length condition. The drawstring may be configured so that a mechanical advantage is obtained by applying tension to the drawstring. The configuration might comprise looping the drawstring at least twice between said points so that drawing the drawstring a certain length will reduce the length of the strip by half that length.

The strip may have a central region removed therefrom and the drawstring may be looped around said central region.

The invention extends to a method of treating vaginal prolapse which comprises attaching a strip of the type defined above between the pelvic floor and the vault, using the drawstring to reduce the length of the strip, thereby pulling the vault towards the pelvic floor, and tying the drawstring off to maintain the strip in its reduced length condition, thereby forming a tie between the vault and the pelvic floor.

In the preferred form of the invention two strips are attached in this manner to the pelvic floor, on opposite sides of the rectum from opposite sides of the vault. The strip or strips are preferably attached to the cardinal ligament area of the vault.

Where the procedure is performed vaginally it will first be necessary to open the posterior floor of the vagina to obtain access to the pelvic floor.

It will be appreciated that the strip of the invention could well have application in surgical procedures in addition to that of treatment of vault prolapse.

These and further features of the invention will be made apparent from the description of preferred embodiments thereof given below by way of example. In the description reference is made to the accompanying drawings, but the specific features shown in the drawings should not be construed as limiting on the invention.

DETAILED DESCRIPTION OF THE EMBODIMENTS

Figure 1:
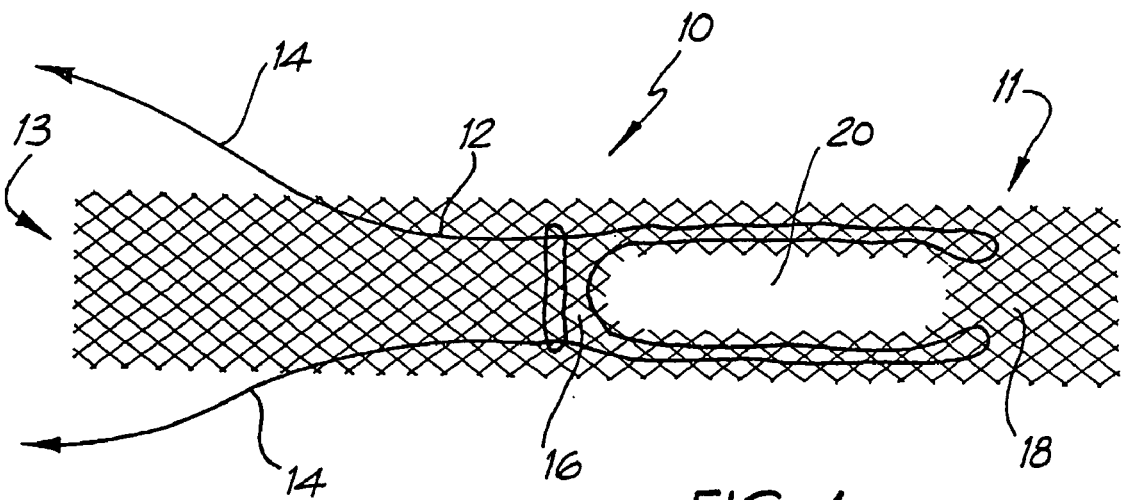
FIG. 1 shows a plan view of a strip of mesh according to the invention.
Figure 2:
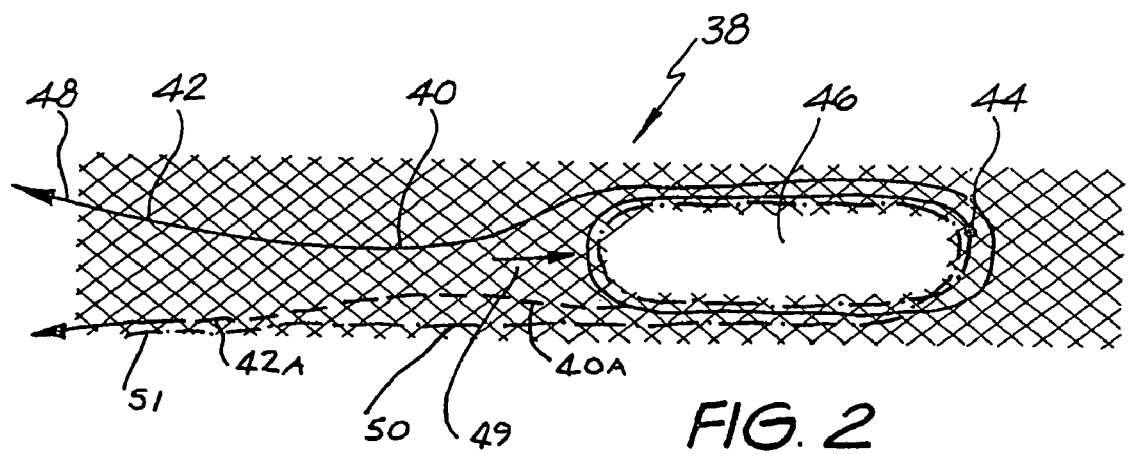
FIG. 2 shows a plan view of another strip of mesh according to the invention.
Figure 3:
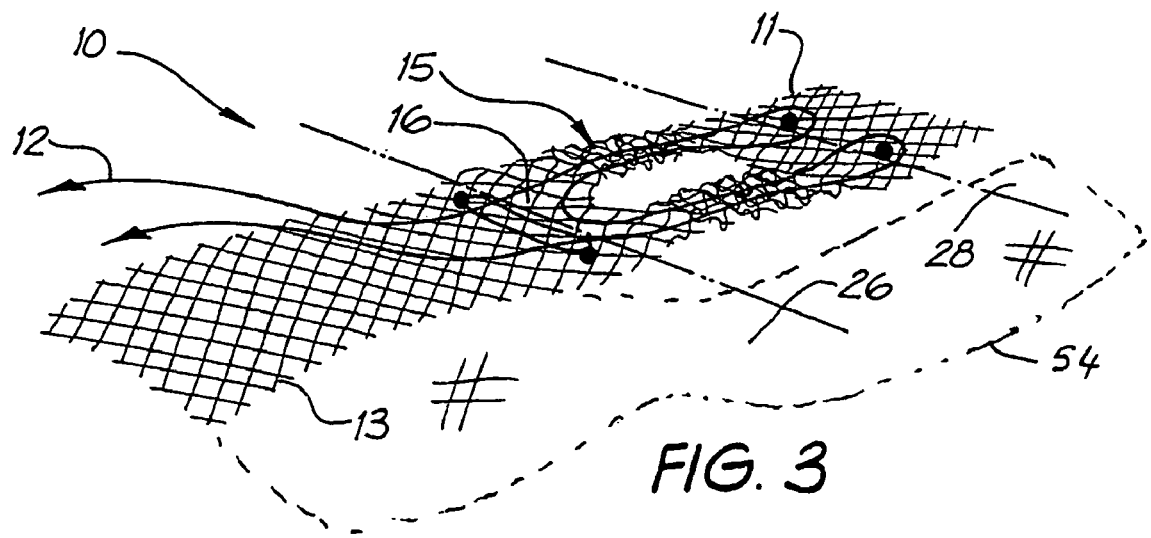
FIG. 3 shows a perspective view of a strip according to the invention fixed in portion between two locations in a body, the strip being in its reduced length condition.

Referring initially to FIGS. 1 to 3, a strip 10 according to the invention is formed of a length of mesh material which conveniently comprises a wide mesh formed of a Vypro thread and is adapted to be left permanently within the body as a permanent ligament. The strip 10 has a first end 11 which in use will be attached to the pelvic floor of a patient, and a second end 13 which in use will be attached to the vaginal wall of the patient. The manner in which the strip will be used is described in more detail below.

A drawstring 12 is threaded in and out though the mesh openings so as to form an M-shaped double loop, with the two free ends 14 of the drawstring extending parallel with each other towards the one end 13 of the strip. The effect of the drawstring being in this double loop configuration is that the drawstring connects together two points of the strip, numbered 16 and 18 in the drawings. It will be appreciated that pulling on the ends 14 of the drawstring will have the effect of shortening the two loops, causing the strip to gather or pleat between the two points 16 and 18, thereby effectively shortening the strip.

The strip has a central portion 20 in which the mesh material has been removed, the central portion being located in the region of the strip between the two points 16 and 18. Removing the mesh from the central portion has the effect of reducing the quantity of mesh material in the region of the strip which is gathered after pulling on the drawstring.

It will be appreciated that the double loop configuration of the drawstring is selected so that a mechanical advantage is obtained when pulling on the drawstring to thereby facilitate the shortening of the strip. Pulling the two ends of drawstring a set length will shorten the strip by half of that length. Of course, other configurations of drawstring threading will achieve a different mechanical effect.

In FIG. 2 a similar strip 38 is depicted to that shown in FIG. 1 but the drawstring 40 has only a single free end 42 whilst the other end 44 is secured to the mesh. The drawstring 40 is threaded through the mesh openings to form one and a half loops around the central opening 46 and pulling on the end 42 in the direction of arrow 48 will cause the drawstring to tighten around the central opening 46 thereby effectively reducing the length of the strip. A disadvantage of this embodiment is that tying off the drawstring is more difficult, but in some applications this might not be a problem and may be advantageous.

FIG. 2 also shows a variation in which the drawstring 40A is not looped back around the opening 46 to terminate at its anchored end 44. Rather, that portion of the drawstring has a free end 42A so that the entire drawstring has a U-shaped configuration. The drawstring may optionally be anchored at the bight of the U. Tightening of the drawstring is achieved by pulling on the free-ends 42 and 42A in the direction of arrows 48 and at the same time pushing on the mesh in the direction of arrow 49. This is achieved by pushing the vaginal wall 26 towards the pelvic floor 28, and thereafter tying off the free ends 42 and 42A of the drawstring.

A yet further embodiment is illustrated in chain outline at 50, and essentially represents a continuation of the drawstring 40 in mirror image having the mechanical advantage of that drawstring configuration with the added advantage of symmetrical gathering up of the mesh and the ability to tie off both free ends 42 and 51.

As shown in FIG. 3 of the drawings the strip 10 is attached via first end 11 to a first location point which, in the treatment of vault prolapse, will be the pelvic floor 28. The other end 13 will be attached to the other attachment point which, in the treatment of vault prolapse, will be the vaginal wall 26. It will be noted that the end 13 comprises a length of mesh material which is about half of the entire length of the strip 10. The drawstring 12 is threaded through the first end 11 of the strip. Clearly, the second end 13 of the strip may be attached at any point along its length so as to be able to accommodate physiological differences in female patients. The commonest point of attachment of the mesh of the vaginal vault is adjacent the central opening 20, that is, at location 16 on the mesh. The mesh may be reinforced at this point to provide for more secure attachment to the vaginal vault. Excess strip material can, if desired, be cut from the end 13 either prior to or during the attachment procedure.

Once the ends 11 and 13 have been attached to their respective locations in the body the drawstring 12 will be pulled up and the two ends tied off. It will be noted from FIG. 3 that the end 11 has been gathered up, considerably reducing the overall length of the strip 10. The gathered portion of the strip is indicated at numeral 15.

Figure 4:
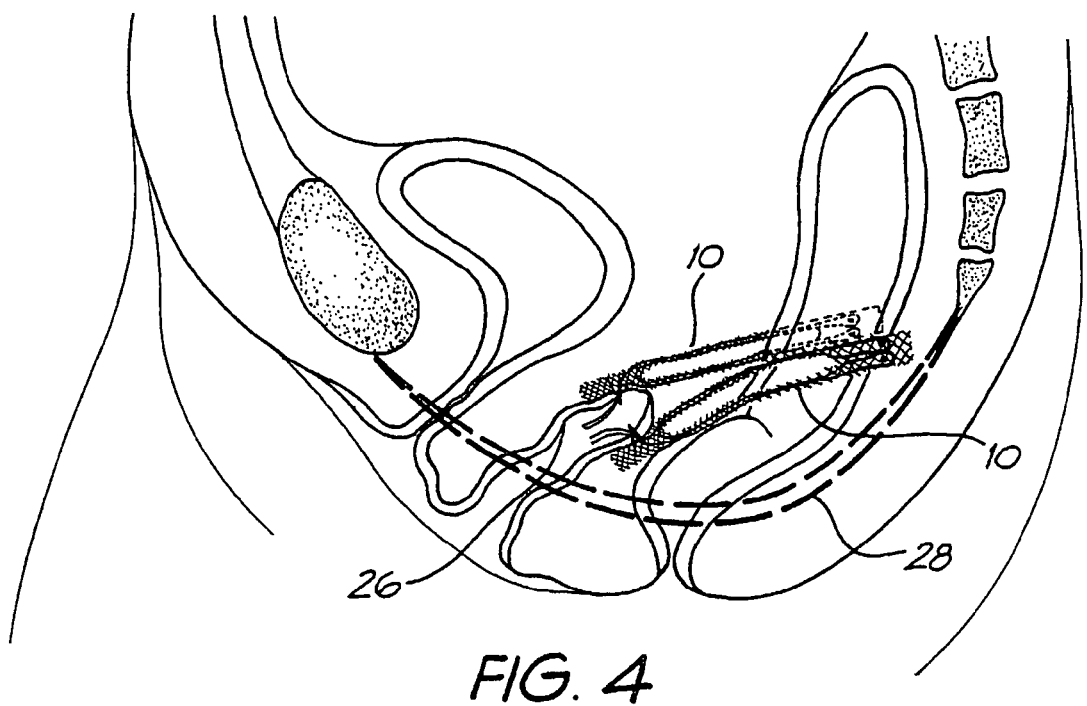
FIG. 4 shows a sectional side view of a patient with two strips according to the invention in place on opposite sides of the vagina.

In use for treatment of vault prolapse, two strips will be connected between opposite sides of the vagina and the pelvic floor. The arrangement is clearly shown in FIGS. 4 and 5 of the drawings.

The first stage of the procedure is to open the posterior vaginal wall 26 to obtain access to the pelvic floor 28. The pelvic floor 28 is exposed on either side of the rectum 30 thereby providing locations where two strips 10 can be attached to the pelvic floor.

The respective ends 11 of the two strips are then attached to the exposed locations on the pelvic floor by suturing. The sutures can simply attach the mesh material itself to the pelvic floor, but preferably the sutures pass around the drawstring so as to form a secure attachment point for the drawstring of each strip. Thereafter the other ends 13 of the two strips are attached to the cardinal ligament area on each side of the vault. Clearly, exactly where along the length of the strip the attachment to the vault is made will depend on the patient's physiology, and typically the actual attachment point will be some distance away from the distal end 13.

Once both ends of both strips 10 have been attached between the pelvic floor and the vault the surgeon will begin closing the posterior vaginal wall. Once partially closed the drawstrings can be used to pull the vault closer to the pelvic floor. Pulling on the drawstrings will, as discussed above, shorten the strips, and since the strips connect the vault to the pelvic floor, the vault will effectively be pulled towards the pelvic floor. Since there are two strips, each with its respective drawstring, the surgeon can ensure that the vagina is correctly aligned and positioned. The drawstrings allow the final alignment and positioning to be done when the vaginal wall incision is partially closed making the whole operation that much easier to perform.

Once the vagina has been pulled into the correct position, the two ends of each drawstring will be tied together, thereby securing each strip in its reduced length condition, permanently holding the vagina in position. The strips are made from a material specifically adapted to be left in place in the body, and will in time form artificial ligaments connecting the vagina to the pelvic floor.

The posterior vaginal wall will then be completely closed and if required the perineal body can be refashioned. Very little if any vaginal mucosa need be excised. As mentioned above, it is desirable that the procedure is performed vaginally since this greatly reduces patient morbidity.

Figure 5:
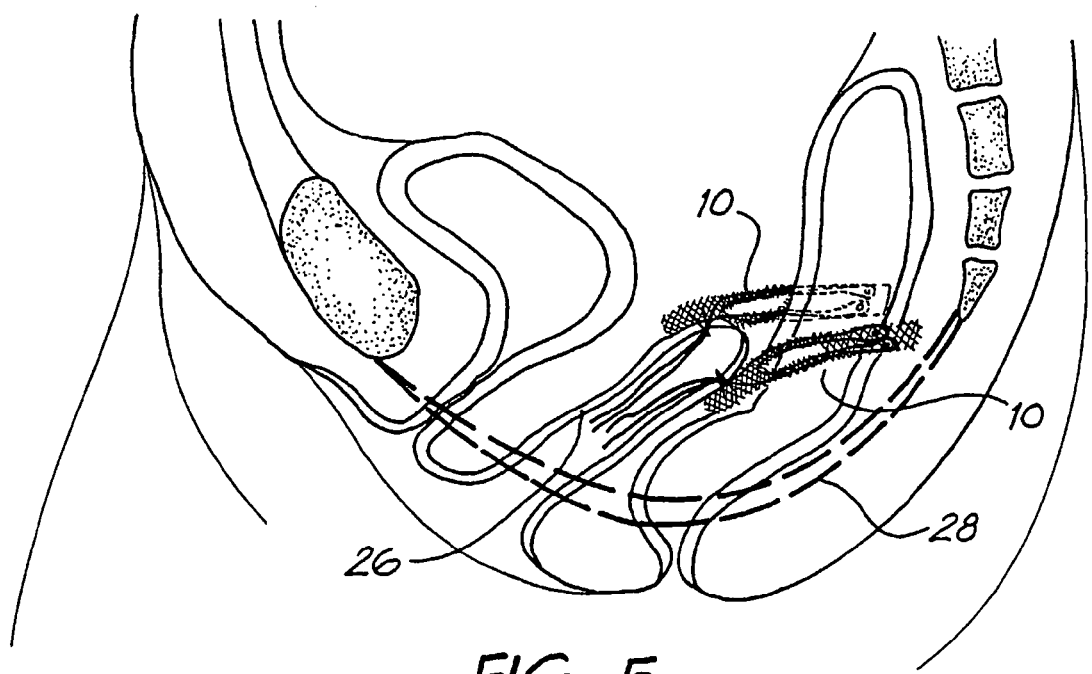
FIG. 5 shows a similar view to that of FIG. 4 but with the strips in their reduced length condition after the drawstrings have been tightened and tied off.

FIG. 5 depicts the two strips in position after the drawstrings have been tied off.

Clearly there may be many variations to the above described embodiment without departing from the scope of the invention. Clearly the strip can be configured differently to that described herein, and can be made of a different material. For example, the two individual strips 10 may converge at their base in the manner indicated in broken outline at 54 in FIG. 3, resulting in Y-shaped configuration with the individual drawstrings being fed through each arm of the Y.

As mentioned above, the drawstring can be threaded differently. However, the advantage of being able to pull the vagina into position at a relatively late stage of the operation will greatly facilitate achieving optimal alignment of the vagina, even though the operation is performed vaginally.

It is envisaged that a mesh or fabric in strip form will best be used to form the apparatus of the invention. However, it should be appreciated that in some applications a strip as such might not be necessary. For example, a longitudinally extending narrow tube might be used in some applications, or a chord-like elongate element might also be used. The drawstring will generally be connected to the ligament defining elongate element in such a way that relative sliding between the drawstring and the elongate element will result in the aforementioned length reduction of the elongate element, as the drawstring has tension applied to it.

The term "drawstring" as used herein is intended to have a broad interpretation and will include any filament that can be used to reduce the length of an element connected between two internal parts within a body. The term "tie" likewise is to be given broad interpretation and is used to describe a connector which is able to act under tension to hold two parts together.

It will be understood that the invention disclosed and defined herein extends to all alternative combinations of two or more of the individual features mentioned or evident from the text or drawings. All of these different combinations constitute various alternative aspects of the invention.

The foregoing describes embodiments of the present invention and modifications, obvious to those skilled in the art can be made thereto, without departing from the scope of the present invention.

The invention claimed is:

1. Apparatus for forming an artificial tie or ligament between a first internal part, and a second, different, internal part, within a mammalian body, the apparatus comprising a strip of flexible material adapted to remain within the body after a procedure has been performed therewith, the strip incorporating a drawstring which extends in a U-shape or loop back configuration between at least two points separated lengthwise along the strip, the drawstring being configured such that when one point has been attached to a first internal part of the body, and the other part point has been attached to a second internal part of the body, a tension applied to the drawstring will assist in causing the length of the strip between the two points to be reduced, and retain the strip in its reduced length condition, thereby forming said artificial tie or ligament between said first and second parts.

2. Apparatus according to claim 1 wherein the strip comprises a fabric or mesh material.

3. Apparatus according to claim 2 wherein the strip is comprised of a light mesh formed of either an absorbable, or a non-absorbable thread.

4. Apparatus according to claim 3 wherein the mesh has openings of between 1 mm and 8 mm in diameter.

5. Apparatus according to claim 3 wherein the drawstring is threaded in and out, through the mesh openings, so that tension applied to the drawstring will tend to cause the strip to adopt a gathered configuration.

6. Apparatus according to claim 5 wherein the drawstring has a central region and two end regions, the end regions being free of the strip, the end regions being adapted to be tied together to hold the strip in its gathered configuration.

7. Apparatus according to claims 5 wherein the drawstring is configured such that mechanical advantage is obtained by applying a tension to the drawstring.

8. Apparatus according to claim 7 wherein the drawstring is looped at least twice between said points so that drawing the drawstring a certain length will reduce the length of the strip by half that length.

9. Apparatus according to claim 5 in which the strip is configured to adopt a gathered configuration by the additional application of force to the mesh in the direction of gathering.

10. Apparatus according to claim 1 wherein a central region of the strip, between said two points, has been removed and the drawstring is looped around said central region.

11. Apparatus according to claim 1 wherein the strip of flexible material has a Y-shaped configuration, with at least one drawstring being carried on each arm of the Y.

12. Apparatus for forming an artificial tie or ligament between different internal parts within a mammalian body, the apparatus comprising a first elongate flexible member, and a second elongate flexible member, each member being formed of a material adapted to remain for at least a significant time within the body, the second elongate flexible member being attached to the first elongate flexible member at at least two points, the attachment at at least one point being a slidable attachment and the second elongate flexible member being in a U-shape or loop back configuration such that tension applied to the second flexible member, relative to the first flexible member will cause the first flexible member to reduce in length, over at least part of its length, opposite end regions of the first elongate member adapted to be attached to different respective parts within a said body.

13. A method of treating vaginal prolapse using at least one elongate flexible member having a drawstring extending between two points separated lengthwise along the member, the method comprising the steps of:

attaching said member between the pelvic floor and the vault, using the drawstring to reduce the length of the member, thereby pulling the vault towards the pelvic floor, and tying off the drawstring to maintain the member in its reduced length condition, thereby forming a tie between the vault and the pelvic floor.

14. A method according to claim 13 wherein two elongate members are attached to the pelvic floor, on opposite sides of the rectum, and to opposite sides of the vault, and the drawstrings of both elongate members are used to reduce the length of their respective elongate members, the drawstrings then being tied off.

15. A method according to claim 13 wherein the procedure is performed vaginally by opening the posterior floor of the vagina to obtain access to the pelvic floor.

16. A method of forming an artificial tie between two internal parts of a mammalian body using at least one elongate flexible member having a drawstring extending between two points separated lengthwise along the member, the method comprising the steps of:

attaching said flexible member between said parts;
using the drawstring to reduce the length of the member, thereby drawing the two parts together; and
tying off the drawstring to maintain the elongate member in its reduced length condition, thereby forming a tie between said parts.

* * * * *